United States Patent [19]

Mian

[11] Patent Number: 5,683,657
[45] Date of Patent: Nov. 4, 1997

[54] DNA MELTOMETER

[75] Inventor: Alec Mian, Cambridge, Mass.

[73] Assignee: Gamera Bioscience, Corp., Cambridge, Mass.

[21] Appl. No.: 464,081

[22] Filed: Jun. 5, 1995

Related U.S. Application Data

[62] Division of Ser. No. 218,030, Mar. 24, 1994.
[51] Int. Cl.⁶ ............................................. G01N 21/25
[52] U.S. Cl. .................. 422/68.1; 422/82.05; 422/82.07; 422/203; 436/94
[58] Field of Search .......................... 422/68.1, 198, 422/223, 251, 82.05, 82.07; 436/94

[56] References Cited

U.S. PATENT DOCUMENTS

| | | | |
|---|---|---|---|
| 4,029,595 | 6/1977 | Ross et al. | 252/299 |
| 4,588,797 | 5/1986 | Curatolo et al. | 526/225 |
| 5,453,461 | 9/1995 | Heiliger et al. | 525/54.1 |

Primary Examiner—Lyle A. Alexander
Attorney, Agent, or Firm—Banner & Witcoff, Ltd.

[57] ABSTRACT

The invention provides an apparatus, termed a DNA meltometer, for the efficient, accurate, and reliable automated performance of DNA sizing, quantitating, probing and sequencing techniques, and methods for using the apparatus in clinical and diagnostic applications for the rapid diagnosis of pathological and disease states.

6 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CAGTCCGTAA CATCTAGCCG AGGAAGACTC TGCCATGCCA AGGAGC    46

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GATCTAGCTA TTAG                                                        14
```

DNA MELTOMETER

This is a divisional of application Ser. No. 08/218,030, filed Mar. 24, 1994.

BACKGROUND OF THE INVENTION

1. Field of the Invention

The invention relates to the fields of medical diagnostics and medical genetics, particularly with respect to molecular biological methods relevant to those fields. In particular, the invention provides methods and an apparatus for sizing, quantitating, probing and sequencing DNA fragments relevant to disease-related genetic polymorphisms and pathological organisms, cells and tissues. Specifically, the invention provides an apparatus, termed a DNA meltometer, for efficient, accurate, and reliable automated performance of DNA sizing, quantitating, probing and sequencing, and methods for using the apparatus in clinical and diagnostic applications for the rapid diagnosis of pathological and disease states.

2. Summary of the Related Art

In the fields of medical genetics and diagnostics, a variety of disease states are characterized by the presence of specific nucleic acids. In inherited diseases, for example, certain specific mutant genes are present in the genomic DNA of an individual. The reduced or absence of expression of the gene product of such specific mutant genes, or the expression of a mutant, non-functional gene product, or a gene product with altered or impaired function, causes or contributes to oven pathology or disease in the individual (see Striver et al., 1989, *The Metabolic Basis of Inherited Disease*, McGraw-Hill, N.Y.). In infectious diseases, the presence of nucleic acid from the disease-causing organism is indicative of the presence of a disease or the imminent or eventual occurrence of the disease even in the absence of immediate symptoms. One important example is infection with human immunodeficiency virus, which infection frequently antedates the appearance of the symptoms of acquired immunodeficiency syndrome by many years (see Fauci, 1988, Science 239: 617–622). A second category of diseases that are not genetic in origin are the so-called environmentally-induced dims. Such diseases are caused by toxic, antigenic or nutritional effects of environmental toxins and other insults on cells and tissues. The resulting molecular pathologies may be identified through the detection of alterations in patterns of gene expression in affected cells and tissues. Thus, specific detection of such indicative nucleic acids has potential as an important diagnostic tool for the clinician.

Over the last decade, research in human genetics has undergone enormous advances, and in over one hundred human diseases a genetic lesion has been identified associated with the disease (Antonarakis, 1989, N. Engl. J. Med. 320: 153–163). The techniques used in the discovery and characterization of these disease-associated DNA polymorphisms include: (1) in vitro amplification of specific nucleic acid sequences, particularly using the polymerase chain reaction; (2) separation and sizing of nucleic acid fragments using gel electrophoresis; (3) detection of particular nucleic acid fragments amongst a multiplicity of such fragments by specific hybridization of nucleic acid bound to various membranes (so-called "Southern" and "Northern" hybridizations); and (4) determination of nucleotide sequences by degradative or, more frequently, synthetic sequencing methods (see Sambrook et al., 1990, *Molecular Cloning: A Laboratory Manual*, 2d ed., Cold Spring Harbor Laboratory Press, Cold Spring Harbor, N.Y. for a detailed description of these techniques).

As robust as these techniques have been in the research laboratory, transfer of these technologies to the clinical lab has proven to be difficult. In particular, automation and standardization of these techniques to routine clinical and diagnostic applications has been slow. This is due in pan to the fact that all of these techniques typically have involved agarose or polyacrylamide gel electrophoresis as a final characterization step. Gel electrophoresis, while effective in the research setting, is cumbersome, difficult to automate and requires skilled laboratory personnel to perform. In addition, gel electrophoresis techniques typically involve the use of hazardous chemicals, such as ethidium bromide (which is mutagenic) and acrylamide (a neurotoxin), radioactivity, and/or hazardous conditions, such as high voltages (up to 4000V) or the use of ultraviolet transilluminators. In addition, visualization of specific DNA fragments separated in gels usually requires photographic equipment, a darkroom, and X-ray film developing equipment, all of which makes these techniques less economical to use and increases the level of skill required to reliably perform these analyses.

There is thus a need in the clinical diagnostic arts for a simple, robust and easily-automated alternative to gel electrophoresis which could be used by technicians having considerably less skill in the molecular biological arts than is required to perform the currently available gel electrophoretic methods. Even within the molecular biological arts, certain areas of ongoing, important research, including the Human Genome Project (see Olson et al., 1989, Science 245: 1434–1435) are limited in the rate at which advances can be achieved by the amount of time consumed using currently-available, electrophoresis-based nucleic acid size separating methods. Advantageous features of an alternative to these methods include rapid "run" times, ease of use, high throughput, and automated operation by conventionally-trained clinical laboratory technical personnel.

BRIEF SUMMARY OF THE INVENTION

The present invention provides a "gel-free" nucleic acid detection and characterization system, comprising an apparatus and methods for using the apparatus to size, quantitate, probe and sequence nucleic acid without the use of gel electrophoresis. The invention provides nucleic acid detection in a single, easy-to-use, automatable instrument, termed a DNA meltometer. The meltometer is comprised of the following components, in operative combination: a thermomodulating chamber in which the temperature can be accurately, reliably and rapidly adjusted to any temperature between about 15° C. and 95°–100° C.; temperature controllers including heating elements and cooling or refrigeration units in thermal contact with the thermomodulating chamber for adjusting the temperature in the thermomodulating chamber; and a detector for detecting thermal denaturation of double-stranded DNA or RNA:DNA hybrids, i.e., for detecting single-stranded DNA or RNA produced as the result of thermal denaturation of double-stranded DNA or RNA:DNA hybrids. Optionally and advantageously, the meltometer is also comprised of a data-processing device and an interface whereby the data-processor controls the operation of the other components of the apparatus and collects, records and stores data produced by operation of the apparatus. Also optionally included in the components of the meltometer is a pump for moving a liquid buffer solution through the thermomodulating chamber, preferably arranged to cause a flow of buffer through the thermomodulating chamber and past the detector; in such embodiments of the apparatus of the invention, the thermomodulating chamber advantageously has a first opening and a second opening, whereby buffer flows into the chamber through the first opening and out from the chamber through the second opening, which second opening is connected with or attached to the detector.

The apparatus and methods provided by the invention are useful for: (a) sizing nucleic acids ranging in length from about 50 to about 500 basepairs (bps) in length; (b) quantitating an amount of a specific DNA fragment, either alone or in a mixture of heterologous DNA fragments; (c) detecting a specific nucleotide sequence of a nucleic acid among a plurality of non-specific nucleotide sequences by hybridization to a sequence-specific nucleic acid probe; and (d) detecting a nested set of extended nucleic acid sequencing oligonucleotides ranging in length from about 20 to about 100 nucleotides, each extended oligonucleotide having at its 3' extent a polymerase chain-terminating compound, thereby providing for gel-free nucleotide sequencing of nucleic acids.

The present invention is based on the following technical considerations. Nuclei acids have conventionally been characterized by gel electrophoresis on the basis of their physical size, the most important parameter of which is length. Apart from physical size, another property characteristic of any double-stranded nucleic acid is the temperature at which the two complimentary strands dissociate from one another. This property, termed the melting temperature, $T_m$, is defined as the temperature at which 50% of the nucleic acid molecules have dissociated into their component single strands. The $T_m$ of a given small (less than approximately 600 basepairs) nucleic acid is known to depend on two factors: the size (i.e., length) of the fragment, and the sequence and base composition of the fragment. Size contributes to $T_m$ because the longer a nucleic acid is, the more hydrogen-bonded basepairs it contains, which thereby require more thermal energy to be broken apart. Base composition effects are due to the fact that G≡C basepairs are more stable than A=T basepairs because they share more inter-strand hydrogen bonds between the basepairs. Base sequence effects are due to the fact that the bases interact with one another within each strand in a manner that stabilizes the double-stranded conformation.

The use of various formulae to predict the $T_m$ of a DNA duplex of known length and base composition is well known in the art. The instant invention for the first time provides an apparatus and methods for using the $T_m$ of a DNA fragment to identify its length and (in some embodiments of the methods of the invention) its base composition.

The effects of base composition and sequence on $T_m$ can be removed by the use of isostabilizing compounds. These compounds bind specifically to GC or AT basepairs, and act to destabilize or stabilize, respectively, the hydrogen bonding between the basepairs. In the presence of isostabilizers, the $T_m$ of some nucleic acid fragments becomes a function solely of its length. In addition, isostabilizers sharpen the melting transition, thereby increasing the resolution of detection of different nucleic acid fragments which differ in length, for example, by even a single nucleotide.

Specific preferred embodiments of the present invention will become evident from the following more detailed description of certain preferred embodiments and the claims.

DETAILED DESCRIPTION OF THE PREFERRED EMBODIMENTS

The present invention provides an apparatus, termed a DNA meltometer, for gel-free sizing, quantitating, probing and sequencing nucleic acid fragments, preferably double-stranded DNA fragments. The DNA meltometer is based on the principle that the $T_m$ of a DNA fragment under the appropriate conditions is essentially a function of the length of the DNA fragment. Methods for sizing, quantitating, probing and sequencing DNA fragments, in the absence or in the presence of isostabilizing compounds, are also provided by the invention.

The apparatus is comprised of an thermomodulating chamber (5 in FIG. 1) for containing a buffer solution of a double-stranded nucleic acid such as DNA wherein the DNA is thermally denatured therein. Exemplary embodiments of such an thermomodulating chamber include a thin-walled polypropylene tube contained within a heating block comprised of a heat-conducting material, which embodiment advantageously is limited to a single use to avoid the possibility of cross-contamination of samples. Another embodiment of the thermomodulating chamber component of the meltometer is a cell or chamber comprised of heat-conducting material and defining a cavity having at least one opening for inserting a sample and flushing such a sample after each sample determination. Advantageously, the thermomodulating chamber of the meltometer has a first and second opening, allowing the flow of a liquid buffer solution, a liquid sample-containing solution or any other liquid solution through the chamber. In such embodiments of the meltometer are included a pump (9 in FIG. 2) for moving buffer from a buffer reservoir (10 in FIG. 2) through the thermomodulating chamber and past a detector (6 in FIGS. 1 & 2). An example of a pump useful in this embodiment of the DNA meltometer is a high pressure liquid chromatography pump (available from Beckman Scientific Instruments, Fullerton, Calif.). In additional embodiments, the thermomodulating chamber is defined by a number of sample wells allowing multiple determinations to be made sequentially or contemporaneously.

Figure 1:
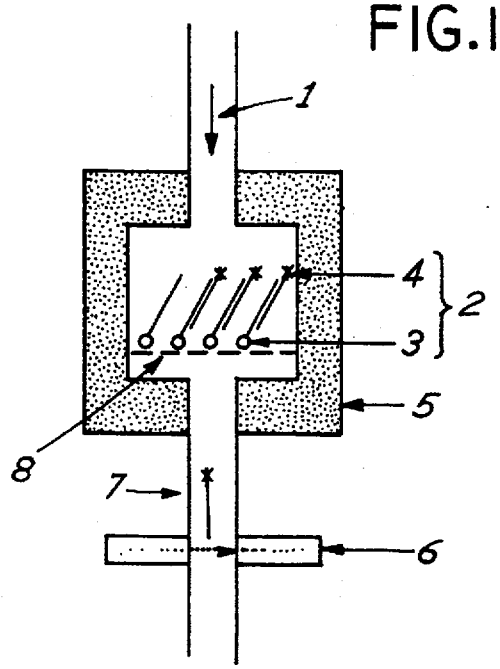
FIG. 1 illustrates the structure and operation of the thermomodulating chamber of the DNA meltometer, wherein 1 represents the direction of flow of temperature-controlled buffer, 2 represents tethered DNA, consisting of 3 an immobilized strand and 4 a detectably-labeled thermally-denatured, detectably-labeled, single-stranded DNA or RNA molecule and 8 represents a tethered DNA retainer.

In certain embodiments, the thermomodulating chamber is also comprised of a double-stranded nucleic acid retainer (8 in FIG. 1). Exemplary retainers include but are not limited to Teflon® filters for retaining nucleic acid fragments that have been tethered to latex beads. Another example of an advantageously-used retainer is an external magnetic field generator for retaining nucleic acid fragments that have been tethered to ferrous metal-binding agents, such as transferrin or paramagnetic beads (available from Dynal, Oslo, Norway).

The thermomodulating chamber of the meltometer is in thermal contact with temperature controlling devices such as heating elements and/or cooling or refrigerating units for regulating the temperature within the chamber. A variety of such temperature regulating units are known to those with skill in this art, including but not limited to metallic heating strips, cooling fans, refrigeration units, and the like. In particular, temperature regulators are known which are capable of regulating temperature to within ±1° C., more preferably ±0.1° C., and most preferably +0.01° C. (an example of which is a temperature controller available from Eppendorf, Hamburg, Germany).

Thermal-denaturation of nucleic acid, comprising the dissociation of a double-stranded nucleic acid into single-stranded DNA or RNA, is detected using a detector (6 in FIGS. 1 & 2) that detects a physical property unique to the single-stranded conformer of a DNA fragment. Such properties may be detected by essentially three categories of detectors: direct detectors, semi-direct detectors and indirect detectors. Direct detection of thermal denaturation can be achieved, for example, using a calorimeter to detect the heat of dissociation released when a double-stranded nucleic acid denatures into its component single strands. Another example of direct detection is spectrophotometric detection. In this detection method, what is detected is the increase in absorbance of ultraviolet light at a wavelength of 260 nm that is associated with thermal denaturation (the so-called denaturation hyperchromicity effect). Such direct methods will be understood by those with skill in the art to be limited by the requirement of nanomoles ($\sim 10^{14}$ molecules) of target nucleic acid.

Semi-direct methods of thermal denaturation detection include detection of the binding or dissociation of single- or double-strand conformation specific dyes and intercalating compounds. Thus, for example, thermal denaturation may be detected by the increase in the effective concentration of a spectrophotometrically-detectable double-strand specific dye, binding moiety or intercalating compound. Typically, these types of dyes absorb or emit light at a certain wavelength in a way that depends on whether or not the dye is bound to, associated with or intercalated into a double-stranded DNA molecule. Using these types of dyes, the amount of the dye that is bound to, associated with or intercalated into a double-stranded DNA molecule can be detected by the increase (or decrease) in absorbance or emission of light at the appropriate wavelength as the DNA molecule is thermally denatured. Alternatively, thermal denaturation may be detected by the decrease in the effective concentration of a spectrophotometrically-detectable single-strand specific dye, binding moiety or intercalating compound. These dyes are similar to double-strand specific dyes in that the amount of light absorbed or emitted at a particular and characteristic wavelength depends on whether or not the dye is bound to, associated with or intercalated into a single-stranded DNA molecule. Thus, using these types of dyes, the amount of the dye that is bound to, associated with or intercalated into a single-stranded DNA molecule can be detected by the increase (or decrease) in absorbance or emission of light at the appropriate wavelength as the amount of single-stranded DNA increases with thermal denaturation of the double-stranded DNA. More complex "sandwich"-type systems are known, wherein additional specific binding components are involved in intermediate steps between thermal denaturation and the increase or decrease in the effective concentration of a detectable dye, binding moiety or intercalator. In such systems, the binding or release of either a dye or an intermediate specific binding moiety is detected spectrophotometrically by the increase or decrease in the effective concentration of the detectable dye.

A variety of useful nucleic acid-specific dye compounds are known, including, for example, ethidium bromide, or preferably, DAPI, Hoechst 33258, and, most preferably, TOTO/YOYO (Molecular Probes, Eugene, Oreg.). The use of this latter dye enables detection of as little as femtomoles ($\sim 10^9$ molecules) of target nucleic acid (see Glazer & Hays, 1992, Nature 359: 8591.

Indirect detection methods include, but are not limited to, fluorescence or infrared spectrophotometry of fluorescently- or infrared-tagged single-stranded DNA or RNA. Fluorescence detection is preferably used in embodiments of the meltometer comprising flow of a liquid buffer solution through the thermomodulating chamber and past the detector, under conditions and using an thermomodulating chamber wherein undenatured nucleic acid is retained within the thermomodulating chamber. An example of such an arrangement is shown in FIG. 1. In this example of indirect detection using the apparatus of the invention, a liquid buffer solution, preferably an aqueous buffer solution such as standard citrate saline (SSC; see Sambrook et al., 1990, ibid.) is made to flow (wherein 1 represents the direction of flow of temperature-controlled buffer) through the thermomodulating chamber 5 at a temperature that is initially below the $T_m$ of the particular DNA fragment of interest. In the chamber is a sample of tethered DNA 2 retained therein by a retainer 8. The tethered double-stranded DNA consists of an immobilized strand 3 and a detectably-labeled, preferably a fluorescently- or infrared-labeled strand 4. As the temperature in the thermomodulating chamber is increased, the DNA denatures at a characteristic temperature (the $T_m$) and the detectably-labeled strand is moved by the flow of buffer from the thermomodulating chamber 5 past a detector 6, where it is detected as a thermally-denatured, fluorescently- or infrared-labeled, single-stranded DNA or RNA molecule 7. The use of fluorescence-based or infrared-based indirect detection methods can enable detection of 1000-2000 molecules in solution (Middendoff et al., 1992, Electrophoresis 13: 487), or even of a single molecule (Davis et al., 1991, GATA 8: 1), theoretically.

In the use of the meltometer provided by the invention, nucleic acid to be sized, quantitated, probed or sequenced is advantageously modified to comprise a tethering molecule on one strand. Incorporation of such a tethering molecule provides a way to retain the double-stranded nucleic acid in the thermomodulating chamber and to prevent detection of undenatured DNA by the detector. This is accomplished by tethering, anchoring or immobilizing the double-stranded nucleic acid inside the thermomodulating chamber. The undenatured DNA may be anchored, tethered or immobilized to the thermomodulating chamber itself, or more preferably to a retainer (8 in FIG. 1) within the thermomodulating chamber. Advantageous combinations of tethering molecules and retainers include but are not limited to biotinylated nucleic acids linked to streptavidin-coated latex or glass beads, and retained within the thermomodulating chamber by a Teflon® membrane. Also included in such advantageous embodiments of the invention are nucleic acids linked to a magnetic metal, with or without the use of a chelating moiety such as porphyrin or ferritin, and retained within the thermomodulating chamber by the application of an external magnetic field. Tethering molecules can be added to the double stranded nucleic acid by replacement synthesis, hybridization, chemical modification or during in vitro chemical synthesis or in vitro amplification.

In the use of the meltometer provided by the invention, nucleic acid to be sized, quantitated, probed or sequenced is advantageously modified to comprise a detectable label on the one strand. Incorporation of such a detectable label provides a way to detect denaturation of the double-stranded nucleic acid. One non-limiting example of a preferred detectable label is a fluorescent label such as fluorescein or rhodamine, or an infrared label such as a polymethine dye. Detectable label molecules can be added to the double stranded nucleic acid by replacement synthesis, hybridization, chemical modification or during in vitro chemical synthesis or in vitro amplification. Also included in this aspect of the invention is the non-covalent incorporation of a detectable label into the double-stranded nucleic acid, for example, intercalation of single-strand or double-strand conformation-specific detectable dyes. Examples of such nucleic acid conformation-specific dye molecules include but are not limited to ethidium bromide, or preferably, DAPI, Hoechst 33258, and, most preferably, TOTO/YOYO.

In addition and advantageously, the solution within the buffer chamber is comprised of a isostabilizing compound. Exemplary isostabilizing compounds include betaine, sarcosine, taurine, glycerol, TMAO, TMACl, TEACl, among others, the isostabilizing properties of which are disclosed in accompanying Table I.

TABLE I

| isostabilizers | compound type | effective molarity | fold sharpening of melting transition | change in Tm of calf thymus DNA (°C.) |
|---|---|---|---|---|
| salts | | | | |
| TMACl[1] | alkylammonium | 3 | 5 | +23 |
| TEACl[1,2] | alkylammonium | 2.4 | 5 | −10 |
| osmolytes | | | | |
| betaine[3,4] | zwitterion | 5.2 | 4 | −15 |
| sarcosine[4] | zwitterion | NA | — | — |
| taurine[4] | zwitterion | NA | — | — |
| TMAO[4] | methylamine | NA | — | — |
| glycerol[4] | polyhydric alcohol | NA | — | — |

Data Sources:
[1]Wood et al (1985) Proc. Natl. Acad. Sci. USA 82: 1585–1588
[2]Melchior, WB and von Hippi PH (1973) Proc. Natl. Acad. Sci. USA 70: 298–302
[3]Rees, et al (1993) Biochemistry 32: 137–144
[4]Yancey et al (1982) Science 217: 1214–1222

Use of such isostabilizing compounds is advantageous because these compounds increase the degree to which the $T_m$ of a nucleic acid is proportional to its length (see Wood et al., 1985, Proc. Natl. Acad. Sci USA 82: 1585–1588). In addition, isostabilizing compounds of the invention act to sharpen the melting transition, i.e. they act to decrease the range of temperature over which a double-stranded nucleic acid changes from being essentially completely double stranded to being essentially completely single stranded (see Rees et al., 1992, Biochemistry 32: 137). This feature is advantageous because it results in increased resolution of different nucleic acids that differ by, at the limit, a single basepair, such as the nested set of extended oligonucleotides which represent the products of a DNA replacement-synthesis sequencing reaction.

Figure 2:
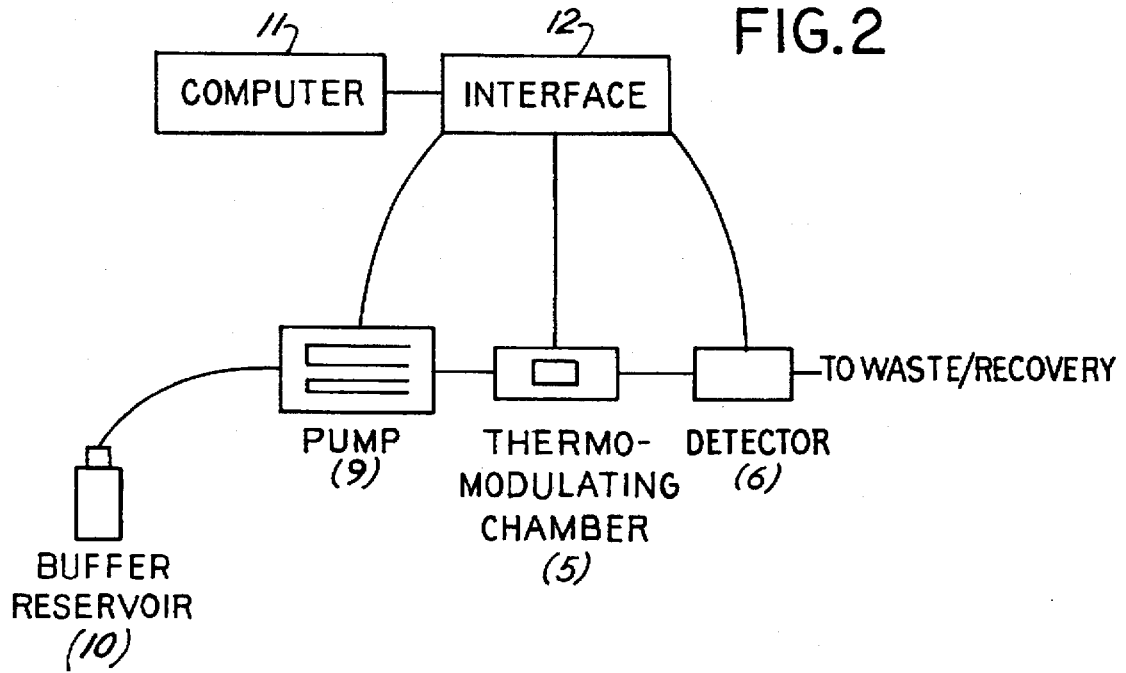
FIG. 2 illustrates an automated embodiment of the DNA meltometer, wherein 5 represents the thermomodulating chamber, 6 represents the detector, 9 represents a pump for moving buffer through the thermomodulating chamber 5, 10 represents a buffer reservoir, 11 represents a data-processor for controlling operation of the apparatus and 12 represents an interface enabling the computer to control operation of the apparatus and to collect and store data produced by the apparatus.

The DNA meltometer is provided in a preferred embodiment as an automated apparatus. A schematic diagram of this embodiment of the meltometer is shown in FIG. 2. In this embodiment, the operational steps are controlled by an interface unit (12 in FIG. 2), preferably an I/O interface such as, for example, an Omega OM-900 unit, controlled by a dam-processor (11 in FIG. 2), such as a computer. Operational steps include control of the temperature regulating units, control of the flow rate of buffer through the thermomodulating chamber, and control of the detection of thermal denaturation by the detector. Also a feature of this preferred embodiment of the meltometer is the use of the computer to acquire, record and store data generated by operation of the apparatus.

The DNA meltometer provided by the invention is useful to enable gel-free sizing, quantitating, probing and sequencing of nucleic acids. The method of sizing a nucleic acid fragment, for example, a DNA fragment, provided by the invention comprises the steps of placing a solution comprising the DNA fragment in the thermomodulating chamber of the meltometer at a temperature less than the thermal-denaturation temperature of the DNA fragment. The temperature of the thermomodulating chamber is then incrementally raised linearly and stringently (±0.01° to 1° C.) at a rate sufficient to detect and resolve denaturation of the DNA fragment. Thermal denaturation of the DNA fragment is thereby detected. In preferred embodiments, one strand of the DNA fragment is linked to a tethering molecule and retained in the thermomodulating chamber via a retainer. The other strand of the fragment is linked to a detectable label that is, for example, a fluorescent label or an infrared label. The thermomodulating chamber is advantageously arranged to have a first and second opening whereby buffer flows through the thermomodulating chamber during the course of thermal denaturation. The thermally-denatured single-stranded, fluorescently- or infrared-labeled DNA molecules flow past the detector as the result of buffer flow from through the thermomodulating chamber, and are thereby detected. In an advantageous modification of this method, a set of DNA size marker fragments are added to the thermomodulating chamber. Such marker fragments are preferably differentially labeled such that the detector can discriminate between each of the marker fragments and the sample DNA fragment. The size of the DNA sample fragment is then determined by comparison with a standard curve prepared using the thermal denaturation temperatures detected for each of the DNA marker fragments.

The method of quantitating a DNA fragment comprises the additional step of calculating the amount of the DNA fragment detected by the detector. In one embodiment, the amount of the fragment detected is quantitated from the total intensity of the detected labeled DNA, using algorithms well-known in the art such as Beers' law to relate the absorbance at a particular wavelength to the amount of the absorbing substance.

The method of probing a nucleic acid fragment, for example, a DNA fragment, to specifically detect a particular DNA fragment from among a multiplicity of DNA fragments provided by the invention comprises the following steps. One strand of each of the multiplicity of double-stranded DNA fragments is linked to a tethering molecule. A solution of a multiplicity of tethered double-stranded DNA fragments is then placed in the thermomodulating chamber of the meltometer in the presence of a retainer, so that the multiplicity of double-stranded DNA fragments are retained in the thermomodulating chamber. The temperature of the thermomodulating chamber is then raised to a temperature sufficient to thermally denature the multiplicity of DNA fragments. Alternatively, thermal denaturation can be accomplished prior to addition of the DNA sample to the thermomodulating chamber. This thermal denaturation results in there being a multiplicity of single-stranded DNA fragments present in the thermomodulating chamber that are targets for later hybridization with a sequence-specific probe. A detectably-labeled nucleic acid probe is then hybridized to the multiplicity of DNA fragments in a hybridization solution, said probe being preferably an oligonucleotide that specifically hybridizes to the particular DNA fragment of interest among the multiplicity of DNA fragments, at a temperature sufficient to allow said hybridization to occur. Excess probe is then removed from the thermomodulating chamber and the temperature in the thermomodulating chamber then incrementally raised linearly and stringently (±0.01° to 1° C.) at a rate sufficient to detect and resolve denaturation of the hybridized oligonucleotide probe from the particular DNA fragment of interest. The thermally-denatured oligonucleotide probe is then detected by the detector. In preferred embodiments, one strand of the multiplicity of DNA fragments is linked to a tethering molecule and retained in the thermomodulating chamber via a retainer. The oligonucleotide is linked to a detectable label that is a fluorescent label or an infrared label. The thermomodulating chamber is arranged to have a first and second opening whereby buffer flows through the thermomodulating chamber during the course of thermal denaturation. The thermally-denatured oligonucleotide, fluorescently- or infrared-labeled probe then flows past the detector as the result of buffer flow through the thermomodulating chamber and is thereby detected.

The method of sequencing a nucleic acid fragment, for example, a DNA fragment, as provided by the invention comprises the following steps. One strand of each of a multiplicity of double-stranded DNA fragments is linked to a tethering molecule and a solution of the multiplicity of tethered double-stranded DNA fragments is placed in the thermomodulating chamber of the meltometer in the presence of a retainer, so that the multiplicity of double-stranded DNA fragments are retained in the thermomodulating chamber. The temperature of the thermomodulating chamber is then raised to a temperature sufficient to thermally denature the multiplicity of DNA fragments. Alternatively, thermal denaturation can be accomplished prior to addition of the DNA sample to the thermomodulating chamber. This thermal denaturation results in there being a multiplicity of single-stranded DNA fragments present in the thermomodulating chamber that are targets for later hybridization with a sequence-specific probe. An oligonucleotide sequencing primer that specifically hybridizes to the DNA fragment at a site in the nucleotide sequence of the DNA fragment adjacent to the site to be sequenced is then annealed to the denatured DNA. This annealing step is performed at a temperature sufficient to allow annealing of the primer to the template DNA to occur. Conventional dideoxynucleotide/ replacement synthesis nucleic acid sequencing reactions are then performed to create a nested set of extended oligonucleotides hybridized to the DNA fragment. The temperature in the thermomodulating chamber is then incrementally raised linearly and stringently (±0.01° to 1° C.) at a rate sufficient to detect and resolve denaturation of each of the nested set of extended oligonucleotides hybridized to the DNA fragment of interest. Each species of the nested set of the extended oligonucleotides is then detected by the detector in a temporal sequence that reflects the nucleotide sequence of the DNA fragment. In preferred embodiments, one strand of the multiplicity of DNA fragments, i.e., the strand complimentary to the oligonucleotide primer, is linked to a tethering molecule and retained in the thermomodulating chamber via a retainer. Each of the nested set of extended oligonucleotides is detectably labeled at the 3' terminus by a fluorescently-labeled or an infrared-labeled dideoxy terminator residue. Optionally and advantageously, each of the dideoxynucleotides can be differentially labeled so as to be individually detectable by the detector. The thermomodulating chamber is arranged to have a first and second opening whereby buffer flows through the thermomodulating chamber during the course of thermal denaturation. Each of the thermally-denatured, fluorescently- or infrared-labeled extended oligonucleotides then flows past the detector as the result of buffer flow through the thermomodulating chamber and is thereby detected in a temporal sequence that reflects the nucleotide sequence of the DNA fragment.

The following Examples are intended to further illustrate certain preferred embodiments of the invention and are not limiting in nature.

EXAMPLE 1

Detecting, Sizing and Quantitating a Specific PCR Product using the DNA Meltometer Polymerase chain reactions are performed using standard techniques. A DNA sample comprising the DNA template to be amplified is mixed at a final concentration of about $10^4$ molecules/reaction in a reaction mixture containing a first oligonucleotide PCR primer of between 15 and 30 nucleotides, that is homologous to a DNA sequence flanking the DNA fragment to be amplified, and that is labeled at the 5' end with a tethering molecule such as biotin. Also in the reaction mixture is a second oligonucleotide PCR primer of between 15 and 30 nucleotides, that is homologous to a DNA sequence flanking the DNA fragment to be amplified, and on the strand opposite to the strand homologous to the first PCR primer, said second PCR primer being labeled at the 5' end with a fluorescent molecule such as rhodamine or fluorescein or an infrared label such as a polymethine dye. Each of the PCR primers is present in the reaction mixture at a final concentration of 1 µM. The reaction mixture also contains: (1) a DNA polymerase such as the thermostable polymerase from *T. aquaticus* (available from Perkin Elmer-Cetus, Emeryville, Calif.) at a final concentration of 1–5U/ reaction; (2) each of 4 deoxynucleotide triphosphates, at a total dNTP concentration of about 200 µM; and (3) a buffer appropriate for the polymerase enzyme used, the buffer typically containing a magnesium ion salt at a concentration of 1–5 mM.

The DNA fragment is amplified following an amplification protocol involving repeated cycles of denaturation of double-stranded DNA, annealing and polymerase-catalyzed extension of the oligonucleotide primers. Amplification is performed for between 10–40 cycles, or until approximately 50–1500 ng (100 picomole) of the DNA fragment have been produced.

The specific DNA fragment is detected using the DNA meltometer as follows. To the PCR reaction comprising the amplified fragment is added a solution containing streptavidin-coated latex beads of a size sufficient to be retained by a Teflon® filter. After binding of the amplified DNA fragments to the latex beads via the biotinylated end of one strand of each fragment, the mixture of latex bead-bound DNA fragments are placed into the thermomodulating chamber of the meltometer, the chamber containing a Teflon® retaining filter. The thermomodulating chamber is equilibrated to a temperature that is less than the thermal denaturation temperature of the DNA fragment before use, and is typically equilibrated to a temperature of 15° C. The pump is used to generate a flow of a buffer solution through the thermomodulating chamber and past a detector, which is calibrated to detect the fluorescently- or infrared-labeled strand of the DNA fragment. Each of the control steps herein described for performance of the DNA fragment detection is preferably performed by a computer in combination with a I/O interface, and the data generated from the detector is also recorded by the computer to form a permanent record of the experiment.

To detect the specific amplified DNA fragment, the temperature of the thermomodulating chamber is incrementally raised linearly and stringently (±0.01° to 1°0 C.) at a rate sufficient to detect and resolve denaturation of the DNA fragment. Optionally, also contained in the thermomodulating chamber is a set of DNA size marker fragments, wherein each fragment is labeled on one strand with biotin and attached thereby to a streptavidin-coated latex bead, and is labeled on the other strand with a fluorescent label or an infrared label. Also optionally contained in the thermomodulating chamber is an amount of an isostabilizing compound. The DNA fragment is detected by the detection of the appropriate signal by the detector. The accuracy of this determination is increased by a comparison of the observed size of the DNA fragment, relative to the DNA size marker fragments, with the expected size of the DNA fragment.

Additionally, the amount of the specific DNA detected can be determined by integration of the total absorbance of labeled DNA fragments detected, using well-known algorithms for such a purpose. The amount of a particular detected fragment will be related to the total absorbance detected at the appropriate wavelength that is specific for that fragment. The use of specific detectable labels is particularly advantageous for this purpose.

EXAMPLE 2

Detecting Specific Hybridization of DNA with an Oligonucleotide Probe using the DNA Meltometer Hybridization of a genetic polymorphism-specific probe with human genomic DNA is achieved as follows. DNA from an individual diagnosed as a carrier of the sickle cell anemia trait [GTG (Glu$^6$)→GAG (Val$^6$) in the human β-globin gene] is digested with a restriction enzyme that does not destroy the polymorphism and that produces a recessed 3' end of each restriction fragment. The DNA is then labeled with ferritin under standard conditions (see Sambrook et al., ibid.), for example, by performing a fill-in reaction of the 3' recessed end using the Klenow fragment of E. coli DNA polymerase I or T4 DMA polymerase and ferritinylated dUTP.

The ferritinylated DNA sample is first denatured and then placed into the thermomodulating chamber of the meltometer, the chamber being supplied with an external magnetic field generator. Said magnetic field is applied throughout the remaining course of the experiment. An oligonucleotide hybridization probe that is homologous to the sickle cell anemia-associated allele of human β-globin and labeled, for example, at the 5' end, with a fluorescent molecule such as rhodamine or fluorescein or an infrared label such as a polymethine dye, is added to the thermomodulating chamber. The temperature of the thermomodulating chamber is then adjusted to a temperature below the thermal denaturation temperature of the oligonucleotide probe with its homologous site in the human genomic DNA of the DMA sample. Hybridization is performed for an appropriate amount of time to allow the maximum amount of specific hybridization to occur, and then excess unhybridized probe is washed from the thermomodulating chamber using a wash solution [typically comprised of 0.1-1% sodium dodecyl sulfate (SDS) in 0.1-2× standard saline citrate (SSC), 1× SSC being comprised of 0.15M NaCl and 0.015M sodium titrate, pH 7.0)]. The pump is used to generate a flow of the washing solution through the thermomodulating chamber and past a detector, which is calibrated to detect the labeled probe. Each of the control steps herein described for performance of the DNA fragment detection is preferably performed by a computer in combination with a I/O interface, and the data generated from the detector is also recorded by the computer to form a permanent record of the experiment.

When the detector no longer detects the passage of any excess unhybridized probe, the temperature of the thermomodulating chamber is incrementally raised linearly and stringently (±0.01° to 1° C.) at a rate sufficient to detect and resolve denaturation of the oligonucleotide probe from the genomic DNA and to allow detection of the denatured DNA probe. The oligonucleotide is detected by the detection of the appropriate signal by the detector. If DNA from an individual heterozygous for the sickle cell anemia trait is used, two distinct thermal denaturation events, occurring at 2 different temperatures, are expected to be detected. The first is the denaturation of the probe from the site of the non-sickle cell anemia-associated allele, which denaturation will occur at the lower temperature because of the presence of a mismatch at the site of the mutation between the genomic DNA and the oligonucleotide probe. The second denaturation event detected will be denaturation of the probe from the site of the sickle cell anemia-associated allele, which denaturation will occur at the higher temperature because of the exact match at the site of the mutation between the genomic DNA and the oligonucleotide probe. Optionally, also contained in the thermomodulating chamber is a set of DNA size marker fragments, wherein each fragment is labeled on one strand with ferritin and retained thereby in the thermomodulating chamber by the externally-applied magnetic field, and is labeled on the other strand with a fluorescent or infrared label. Also optional contained in the thermomodulating chamber is an amount of an isostabilizing compound. The accuracy of this determination is increased by a comparison of the observed size of the DNA fragment, relative to the DNA size marker fragments, with the expected size of the DNA fragment.

EXAMPLE 3

DNA Sequencing using the DNA Meltometer

Dideoxynucleotide/replacement synthesis nucleic acid sequencing of a site of a genetic polymorphism is performed, and a nested set of extended oligonucleotides detected using the DNA meltometer as follows. DNA from an individual diagnosed as a carrier of the genetic polymorphism that causes cystic fibrosis (deletion of the three-base codon encoding Phe$^{463}$ in the cystic fibrosis transmembrane regulator gene) is digested with a restriction enzyme that does not destroy the polymorphism and that produces a recessed 3' end of each restriction fragment. The DNA is then labeled with biotinylated dUTP by fill-in reaction of the 3' recessed end using the Klenow fragment of E. coli DNA polymerase I or T4 DNA polymerase, under standard conditions (see Sambrook et al., ibid. for details of this protocol). Alternatively, a DNA fragment encompassing the site of the genetic polymorphism is produced by in vitro amplification, for example, as described in Example 1.

The biotinylated DNA sample is then denatured and mixed with streptavidin-coated latex beads and then placed into the thermomodulating chamber of the meltometer, the chamber containing a Teflon® retaining filter. A DNA sequencing oligonucleotide primer that hybridizes to a site flanking the polymorphism in the cystic fibrosis-associated DNA fragment is then added to the thermomodulating chamber. A mixture of a DNA polymerase, the appropriate buffers and unlabeled dNTPs, and each of four differentially fluorescently- or infrared-labeled dideoxynucleotide triphosphates is then added to the thermomodulating chamber, at a temperature that allows the sequencing primer to anneal and the polymerase to incorporate dNTPs and ddNTPs into a set of extended oligonucleotides encompassing the cystic fibrosis polymorphic site. After an appropriate amount of time to allow the maximum amount of oligonucleotide extension to occur, the excess sequencing reaction mixture is flushed from the thermomodulating chamber using the pump to generate a flow of washing solution as in Example 2 above through the thermomodulating chamber and past a detector, which is calibrated to detect each of the labeled ddNTPs. Each of the control steps herein described for performance of the DNA fragment detection is preferably performed by a computer in combination with a I/O interface, and the data generated from the detector is also recorded by the computer to form a permanent record of the experiment.

When the detector no longer detects the passage of any excess free ddNTPs, the temperature of the thermomodulating chamber is incrementally raised linearly and stringently (±0.01° to 1° C.) at a rate sufficient to detect and resolve denaturation of each of the nested set of extended oligonucleotides hybridized to the DNA fragment of interest and to allow detection of the differentially-labeled extended oligonucleotide primers. The extended oligonucleotides are detected by the detection of the appropriate signal by the detector. The DNA sequence is determined by the temporal sequence of the detected signal past the detector. Optionally contained in the thermomodulating chamber is an amount of an isostabilizing compound.

A theoretical thermal denaturation profile for sequencing of the sequence CAGTCCGTAACATCTAGCCGAGGAA-GACTCTGCCATGCCAAGGAGC (SEQ ID No.: 1) using the oligonucleotide primer GATCTAGCTATTAG (SEQ ID No. :2) is shown in Table II. The data in this Table were derived as follows. By analyzing nearest-neighbor thermodynamic parameters (see Breslauer et al., 1986, *Proc. Natl. Acad. Sci. USA* 83: 3746), the increase in $T_m$ (in °C.) of the sequence was determined as single nucleotides were added to the oligonucleotide primer. As can be seen in the Table, in theory about 60 basepairs of DNA sequence can be read using the DNA meltometer over a thermal denaturation profile of 22.5° C. →82.6° C., particularly in view of the fact that temperature regulators are commercially available having a precision of ±0.01° C.

TABLE II

| Tm °C. | | 22.5 | 27.0 | 29.9 | 32.2 | 35.1 | 40.2 |
|---|---|---|---|---|---|---|---|
| sequence→ | gatctagctattag | c | a | g | t | c | c |
| fragment size | | 15 | | | | | 20 |
| 45.8 | 47.1 | 47.5 | 49.2 | 50.2 | 52.7 | 53.2 | 54.7 | 56.9 | 57.9 |
| g | t | a | a | c | a | t | c | t | a |
| | | | | 25 | | | | | 30 |
| 58.7 | 61.1 | 63.3 | 66.0 | 67.0 | 67.4 | 69.1 | 70.0 | 70.4 | 70.6 |
| g | c | c | g | a | g | g | a | a | g |
| | | | | 35 | | | | | 40 |
| 71.4 | 71.6 | 71.8 | 72.5 | 72.7 | 73.8 | 75.1 | 76.3 | 77.3 | 77.4 |
| a | c | t | c | t | g | c | c | a | t |
| | | | | 45 | | | | | 50 |
| 77.5 | 78.5 | 79.5 | 80.4 | 80.5 | 80.5 | 81.3 | 81.7 | 81.7 | 82.6 |
| g | c | c | a | a | g | g | a | g | c |
| | | | | 55 | | | | | 60 |

It should be understood that the foregoing disclosure emphasizes certain specific embodiments of the invention and that all modifications or alternatives equivalent thereto are within the spirit and scope of the invention as set forth in the appended claims.

---

We claim:

1. An nucleic acid analysis apparatus comprising, in combination, a thermomodulating chamber, wherein a temperature is defined, and wherein the thermomodulating chamber comprises a first opening and a second opening, wherein each of the openings is connected with a pumping means for passing a buffer solution through the thermomodulating chamber;

heating and cooling means that are in thermal contact with the thermomodulating chamber, for controlling the temperature of the thermomodulating chamber further comprising a nucleic acid retaining means; and a detecting means for detecting thermally-denatured double-stranded DNA at a temperature that is about the $T_m$ of each nucleic acid to be analyzed, wherein the detecting means is connected to one of the openings in the thermomodulating chamber to allow the buffer solution to flow from the thermomodulating chamber and past the detecting means, and thereby sizing, quantitating, probing or sequencing the nucleic acid.

2. The apparatus of claim 1 wherein the detecting means is a fluorescence detector.

3. The apparatus of claim 1 wherein the detecting means is an ultraviolet spectrophotometer.

4. The apparatus of claim 1 wherein the nucleic acid retaining means comprises means for retaining DNA fragments labeled with a tethering molecule.

5. The apparatus of claim 4 wherein the double-stranded DNA retaining means is a Teflon® filter.

6. The apparatus of claim 4 wherein the double-stranded DNA retaining means is an externally-applied magnetic field.

* * * * *

UNITED STATES PATENT AND TRADEMARK OFFICE
CERTIFICATE OF CORRECTION

PATENT NO. : 5,683,657 Page 1 of 1
APPLICATION NO. : 08/464081
DATED : November 4, 1997
INVENTOR(S) : Mian It is certified that error appears in the above-identified patent and that said Letters Patent is hereby corrected as shown below:

Title page, item 62 should read as follow:
Division of Ser. No. <u>08/218,030,</u> ~~218,030~~, Mar. 24, 1994.

Signed and Sealed this

Twenty-ninth Day of January, 2008

JON W. DUDAS
*Director of the United States Patent and Trademark Office*